United States Patent [19]

Steltenkamp et al.

[11] Patent Number: 4,676,915

[45] Date of Patent: * Jun. 30, 1987

[54] ANTISTATIC COMPOSITION AND DETERGENT COMPOSITIONS CONTAINING ANTISTATIC COMPONENTS

[75] Inventors: Robert J. Steltenkamp, Somerset; Michael A. Camara, Jackson, both of N.J.

[73] Assignee: Colgate-Palmolive Company, New York, N.Y.

[*] Notice: The portion of the term of this patent subsequent to Oct. 28, 2003 has been disclaimed.

[21] Appl. No.: 745,731

[22] Filed: Jun. 17, 1985

Related U.S. Application Data

[63] Continuation-in-part of Ser. No. 716,871, Mar. 27, 1985, and a continuation-in-part of Ser. No. 734,508, May 16, 1985, Pat. No. 4,619,775.

[51] Int. Cl.$^4$ ............................................ D06M 3/30
[52] U.S. Cl. ..................... 252/8.8; 252/525; 252/541; 252/544
[58] Field of Search ............... 252/8.8, 541, 544, 525; 546/153; 260/404.5

[56] References Cited

U.S. PATENT DOCUMENTS

| | | | |
|---|---|---|---|
| 3,539,629 | 11/1970 | MacKellar et al. | 564/153 |
| 4,075,130 | 2/1978 | Naylor et al. | 252/548 |
| 4,417,995 | 11/1983 | Lips et al. | 252/8.8 |
| 4,440,666 | 4/1984 | Miller et al. | 252/8.55 |
| 4,497,715 | 2/1985 | Bauman | 252/8.8 |

*Primary Examiner*—A. Lionel Clingman
*Assistant Examiner*—Hoa Van Le
*Attorney, Agent, or Firm*—Herbert S. Sylvester; Murray M. Grill; Norman Blumenkopf

[57] ABSTRACT

An antistatic composition, useful for addition to laundry detergents, shampoos and other preparations for treating fibrous and other materials to diminish tendencies thereof to accumulate electrostatic charges, comprises an amide of trialkylacetic acid and/or an amide of isostearic acid, and a quaternary ammonium salt in a certain range of proportions, with the proportion of amide(s) being greater than that of quaternary ammonium salt. The antistatic composition and the components thereof, in described proportion, are compatible with anionic detergents and other anionic compounds and good antistatic effects are obtainable on washed laundry, dryer-treated laundry and on shampooed hair when the antistatic composition or the components thereof is/are included in the laundry detergent composition, in the dryer product or in the shampoo, and such effects are obtained without the disadvantages attendant the presence of quaternary ammonium halide in anionic synthetic organic detergent based laundry detergent compositions and shampoos in sufficient proportion for the quaternary ammonium halide to make washed laundry or shampooed hair antistatic.

18 Claims, No Drawings

ANTISTATIC COMPOSITION AND DETERGENT COMPOSITIONS CONTAINING ANTISTATIC COMPONENTS

This application is a continuation-in-part of each of our previously filed patent applications Ser. Nos. 716,871, filed Mar. 27, 1985, and 734,508, filed May 16, 1985, now U.S. Pat. No. 4,619,775. This application is also related to U.S. Pat. No. 4,497,715, issued to Robert A. Bauman on Feb. 25, 1985, and U.S. patent application Ser. No. 740,697, filed June 3, 1985 by Clarence R. Robbins and Robert J. Steltenkamp, (the latter being one of the present co-inventors), for CONDITIONING OF HAIR WITH AMIDES OF TRIALKYLACETIC ACIDS.

This invention relates to antistatic compositions. More particularly, it relates to such compositions which comprise an amide of trialkylacetic acid and/or an amide of isostearic acid, and a quaternary ammonium salt, in a certain range of proportions, with the proportion of amide(s) being greater than that of quaternary ammonium salt(s), which compositions are useful antistatic additives for detergent compositions, shampoos and other fiber conditioning products to diminish the tendency of fibrous materials treated with such non-antistatic products to accumulate electrostatic charges. The invention also relates to built synthetic organic laundry detergent compositions, hair shampoos and other compositions and preparations for treating laundry and hair, which compositions and preparations include the components of the described antistatic compositions and are capable of making antistatic those materials which are treated with such compositions.

It has been known for years that quaternary ammonium salts are antistatic agents (antistats). A classic use of such products is in a suitable solution or suspension from which they are applied, as by a spray, to new rugs of synthetic organic polymeric materials, which otherwise would tend to accumulate electrostatic charges and cause crackling noises, sparks and shocks when walked on (especially when "scuffed"). Quaternary ammonium salts have been incorporated in papers, cloths and sponges for use in automatic laundry dryers, and during the drying operation such salts transfer to the tumbling laundry and decrease the tendency of such washed laundry (especially if it is completely or partially of synthetic organic polymeric material, such as nylon or polyester) to accumulate electrostatic charges during the drying operation. Also, the quaternary ammonium salts are sufficiently substantive to fibrous synthetic organic polymeric materials to be adsorbed onto such materials during washing of laundry with a detergent composition containing such "quat(s)". The quaternary ammonium salts, although good antistats, are disadvantageous in laundry compositions based on anionic detergents and in compositions containing fluorescent brighteners and similar dyes that can react with the cationic portion of the quaternary ammonium compounds to form water insoluble reaction products, which can produce greasy stains on laundry and can adversely affect detergency, brightening and dyeing properties of the respective products. Accordingly, the present invention is of importance because the amides of the compositions thereof and in such products, are non-reactive with anionic detergents, fluorescent brighteners and dyes, and the lesser proportion of quat present in the invented compositions and products has a less significant negative effect on detergency, brightening and dyeing characteristics. In fact, the combination of quat and amide of the types described herein results in improved antistatic action, compared to the same proportion of amide(s) alone, and is of fewer negative properties or a lower level thereof than a proportion of quaternary ammonium salt sufficient to produce the same antistatic characteristics in treated materials.

In accordance with the present invention an antistatic composition comprises an amide of trialkylacetic acid and/or an amide of isostearic acid, and a quaternary ammonium salt, with the proportion of amide(s) being from 2 to 10 times that of quaternary ammonium salt. In a preferred embodiment of the invention such composition consists essentially of the described amide(s) and quaternary ammonium salt(s), in the proportions given. Also within the invention are detergent compositions, in particulate, solid, gel or liquid state, including hair shampoos, hair rinses, laundry dryer products (usually impregnated papers, cloths or sponges) and other preparations containing at least two of the described antistatic components (amide and quat), and processes in which such compositions and/or components are employed.

The amides employed in the compositions and processes of the present invention include those of trialkylacetic acid (neoalkanoic acid) and mono alk(en)yl amines or polyamines, and amides of isostearic acid. Such amides of trialkylacetic acid are described in U.S. patent applications Ser. Nos. 716,871 and 734,508 filed on Mar. 27, 1985 and May 16, 1985, respectively, by Robert J. Steltenkamp and Michael A. Camara, as co-inventors, the disclosures of which applications are hereby incorporated herein by reference. In Ser. Nos. 716,871 and 734,508 there are disclosed new compounds which are monoamides of trialkylacetic acid (or neoalkanoic acid) and polyamides thereof, respectively. In U.S. Pat. No. 4,497,715 N-alkyl isostearamides are disclosed.

The amides of trialkylacetic acid, called trialkylacetamides, may be monoamides of a trialkylacetic acid of 5 to 16 carbon atoms and a mono-N-higher alk(en)yl amine, or polyamides of such a trialkylacetic acid and a polyamine wherein the trialkylacetic acid moieties are of 1 to 10 carbon atoms in each of the alkyls thereof and in which each of the polyamine moieties contains from 2 to 5 amino groups. Also useful amides in the present invention are the N-alkylisostearamides represented by the structural formula:

RCONHR' wherein RCO is derived from isostearic acid, and R' is a primary aliphatic saturated or unsaturated hydrocarbon chain containing 1 to 18 carbon atoms.

The N-alkylisostearamides of the present invention can generally be prepared by the conventional methods for amide synthesis. Isostearic acid may be converted to the acid chloride by reaction with thionyl chloride which acid chloride may then be added to a primary amine, dissolved in a solvent such as water, ether or methylene chloride, to form the amide. The secondary amide product is isolated as a viscous liquid or waxy solid, depending on its molecular weight.

More specifically, the present N-alkylisostearamides are prepared from known starting materials by means of a twostep process, first converting isostearic acid, which is a mixture of branched chain isomers of stearic acid of the formula:

C₁₇H₃₅COOH having primarily methyl branching, to the isostearoyl chloride by reacting with thionyl chloride, and then reacting said isostearoyl chloride with a primary aliphatic amine containing to 18 carbons, often preferably 10 or 12 to 18 carbon atoms. These reactions may be represented by the following equations, wherein R and R' are as aforedefined:

1. RCOOH + SOCl₂ $\xrightarrow{\text{dimethyl formamide}}$ RCOCl + HCl + SO₂

2. RCOCl + R'NH₂ ⟶ RCONHR' + HCl

The conversion of the isostearic acid to the isostearoyl chloride is preferably conducted in the presence of dimethyl formamide, which acts as a catalyst in this reaction. Since the amide reaction is exothermic, cooling may be desirable in order to control the temperature. This reaction is preferably conducted in the presence of any non-reactive solvent, such as water, methylene chloride, methyl or ethyl ether, benzene, chloroform or the like, and in the presence of any tertiary amine such as trimethyl amine, pyridine and preferably triethylamine, which reacts with the acid byproduct formed during this reaction. The reaction mixture may be washed successively with water or alcohol/water mixtures, dilute acid and water to remove any unreacted starting material, and may be dried over Na₂SO₄ or similar neutral salt. The solvent is removed, preferably by evaporating in vacuum. The resultant N-alkylisostearamides are liquids, oils or solids, and usually are oily liquids or pasty solids or near-solids.

In addition to the isostearamides, other amides that are useful in the practice of the present invention are the monoamides and polyamides of neoalkanoic acids. The acid moieties of some preferred monoamides used in this invention, higher alkyl and alkenyl [or alk(en)yl] neoalkanoamides of neoalkanoic acids (or of trialkylacetic acids), have 5 to 16 carbon atoms, and preferably such moieties contain from 7 to 14 carbon atoms. Although some branching of the hydrocarbyls is acceptable under certain circumstances, it is preferable that the alkyl and alkenyl groups be substantially or essentially linear, as in tallowalkyl neodecanoamide, and more preferably, they will be linear. Among the more preferable of such neoalkanoamides are those wherein the alkyl or alkenyl is higher, of 8 to 20 carbon atoms, often preferably 12 to 18 carbon atoms, such as may be derived from coconut oil, tallow or hydrogenated tallow or other oil or fat. The mentioned higher alkyls are herein referred to as cocoalkyl, tallowalkyl and hydrogenated tallowalkyl, respectively. It should be noted that in this usage "alkyl" may be inclusive of hydrocarbyl groups containing minor unsaturation, as in tallowalkyl, which contains a minor proportion of monounsaturated C₁₇H₃₃ alkene. However, to avoid any misinterpretation, usually reference herein will be to alk(en)yl, which includes both saturated and unsaturated hydrocarbyl.

Neodecanoic acid, which is a preferred neoalkanoic acid, for making the described neoalkanoic amides, which is available commercially from Exxon Chemical Americas in prime and technical grades, is synthesized by reacting a branched nonene and carbon monoxide under high pressure at an elevated temperature in the presence of an aqueous acidic catalyst (Koch reaction).

The general mechanism involved includes generation of a carbonium ion followed by complexation with carbon monoxide and the catalyst to form a "complex", which is subsequently hydrolyzed to generate the free acid. The formula of the free acid is:

$$R-\underset{\underset{R''}{|}}{\overset{\overset{R'}{|}}{C}}-COOH,$$

wherein R and R' may be different from definitions previously given, and wherein the number of carbon atoms in R+R'+R'' is 8; about 31% of the neodecanoic acid is of a structure wherein R' and R'' are both methyl and R is hexyl; about 67% is of a structure wherein R' is methyl, R'' is of a carbon atoms content greater than that of methyl and less than that of R, and R is of a carbon atoms content less than that of hexyl and greater than that of R''; and about 2% is of a formula wherein R' and R'' are both of a carbon atoms content greater than that of methyl and less than that of R, and R is of a carbon atoms content less than that of hexyl and greater than those of R' and R''. The dissociation constant (Ka) of neodecanoic acid is 4.20×10⁻⁶. Among other neoalkanoic acids that are available may be mentioned others in the 5 to 16 carbon atoms content range, such as neopentanoic, neoheptanoic, neononanoic, neodecanoic, neododecanoic, neotridecanoic and neotetradecanoic acids.

To make the mononeoalkanoamides used in the practice of this invention the neoalkanoic acid, such as neodecanoic acid, may be reacted directly with a higher alkyl- or alkenyl amine [alk(en)yl amine] which is very preferably a linear primary amine, R'''NH₂, but also may include slightly branched alkyls having less than 10 or 20% of their carbon atoms contents in branch(es), e.g., as in 2-methyl heptadecyl. The higher alkylamines and alkenylamines employed will normally be of a number of carbon atoms in the range of 8 to 20, often preferably 12 to 18, but may include compounds of more or fewer carbon atoms too, providing that the amides made possess the desired properties, as described herein. Among the more preferred of the amine starting materials are cocoalkyl amine, tallowalkyl amine (which contains a minor portion of oleyl amine), and hydrogenated tallowalkyl amine. Such materials are produced from vegetable and animal sources, and amides made from them have been found to be excellent fiber conditioning agents, which are compatible with anionic detergents. Also notable as useful amine starting materials are oleyl amine and octyl amine.

The invented amides, which are of the formula:

$$R-\underset{\underset{R''}{|}}{\overset{\overset{R'}{|}}{C}}-\overset{\overset{H}{|}}{\underset{}{C}}ON-R''',$$

may be made by reacting a neoalkanoyl chloride with a higher alkyl or alkenyl amine, R'''NH₂, but a less costly synthesis is directly from the neoalkanoic acid by reacting it with such amine at an elevated temperature. The melting points of the products will normally be low, so that the products will desirably be liquids at room temperature or at normal use temperatures. The melting points of the cocoalkyl-, tallowalkyl- and hydrogenated tallowalkyl neodecanoamides are <0° C., 15°–17° C. and 45° to 49° C., respectively while those of the octyl, oleyl, palmityl and stearyl counterparts are <0° C., 5° to 6° C., 37° to 38° C. and 35° to 40° C., respectively. Melting points for the other neoalkanoamides of 5 to 16 carbon atoms in the neoalkanoic acid will be in the <0° C. to 50° C. range and preferably the amides will be oily liquids or plastic or flowable materials at temperatures of 40° C. or less.

Although the described N-higher alkyl neodecanoamides are among the preferred embodiments of the present invention, other highly branched acids may also be employed for the manufacture of higher alkyl amide antistats. When neopentanoic acid is employed (it is of the formula

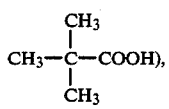

for the manufacture of N-higher alkyl neopentanoamides, useful antistatic effects are obtainable from the invented compositions but not to the extent realized for the higher alk(en)yl neodecanoamides. Normally the neoacid employed to make the hair conditioning monoamides will be of 5 to 16, preferably 7 to 14 carbon atoms, and such acids are obtainable by the described process when highly branched $C_4$–$C_{15}$ or $C_6$–$C_{13}$ olefins are employed as starting materials in the Koch reaction.

In addition to the previously described monoamides of neoalkanoic acids, also useful in the invented processes and compositions are polyamides of trialkylacetic acid(s) and polyamine(s), such as those wherein the trialkylacetic acid moieties are of 1 to 10 carbon atoms in each of the alkyls, R, R' and R", of the formula

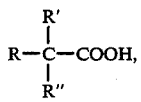

and the polyamine moieties contain from 2 to 5 amino groups. Preferred polyamides are those wherein the sum of the carbon atoms of the alkyls of each of the trialkylacetic acid moieties is from 3 to 12, more preferably 4 to 9, and the polyamine moiety is a diamine or triamine moiety with an alkylene group of 2 to 10 carbon atoms and/or polyoxyalkylene group(s) connecting the amide groups of the polyamide. In such compounds the oxyalkylene of the polyoxyalkylene groups is of 2 to 4 carbon atoms, more preferably three, the number of such oxyalkylene groups in each polyoxyalkylene group is from 1 to 40, more preferably 2 to 10, and the alkylene group of the polyoxyalkylene alkylene is of 1 to 10 carbon atoms, more preferably 2 to 3.

In this description the various polyamides, component groups, moieties, substituents thereof and reactants will often be referred to in the singular, as will be components of the described compositions and materials employed in the described processes, but it should be understood that various mixtures of two or more of the same and/or different types thereof are also intended. When reference is made to "neoalkyl" or trialkylmethyl, that is intended to describe the "residue" of a neoalkanoic acid after removal of the carboxyl therefrom.

As was previously mentioned, the polyamines that may be reacted with trialkylacetic acid to make the present polyamides are preferably diamines or triamines. The triamines that may be used to make the polyamides that are employable according to the present invention are preferably alkylene polyoxyalkylene triamines, such as those sold by Texaco Chemical Company under the trademark Jeffamine. Of such materials Jeffamine T-403, which is of the formula

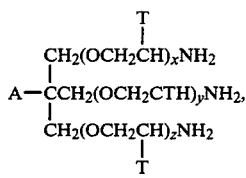

wherein A=ethyl, T=methyl, and $x+y+z=5.3$, is preferred. The diamines that are useful to making the diamides employed in this invention have both amino groups thereof connected by an alkylene polyoxyalkylene moiety or by lower alkylene groups. Of the commercially available diamines containing oxyalkylene groups the Jeffamines are preferred, and the formula of such compounds is

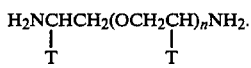

In that formula, while T may often be hydrogen or lower alkyl, for the Jeffamines it is methyl and n is in the range of 2 to 10, more preferably 2 to 7. Among such compounds which may be employed are: Jeffamine D-230, wherein n averages about 2.6; Jeffamine D-400, wherein n averages about 5.6; and Jeffamine D-2,000, wherein n averages about 33.1. Of these diamines the more preferred are Jeffamine D-230 and Jeffamine D-400. Among the non-alkoxylated diamines that are useful are alkylene diamines of 2 to 6 carbon atoms, such as ethylene diamine, propylene diamine, and hexamethylene diamine.

Instead of using neoalkanoic acids for the manufacture of the present monoamides and polyamides, the corresponding acyl halides may be employed. Such materials are normally used as acid chlorides, such as neodecanoyl chloride, which is available from the Lucidol Division of Pennwalt Corporation, and is described in their product bulletin entitled *Acid Chlorides*, printed in Sept., 1982, which also generally describes reactions of acid chlorides with amines.

The polyamides of the present compositions and processes include those of alkoxyamines, such as:

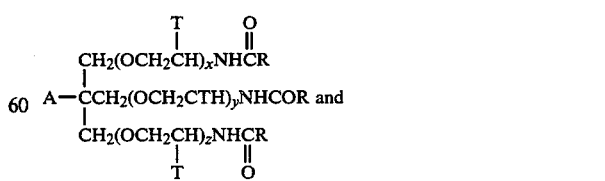

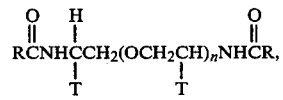

wherein A is alkyl of 1 to 20 carbon atoms or hydrogen, T is methyl or hydrogen, R is a neoalkyl of 4 to 13 carbon atoms, n is from 1 to 40, and x, y and z are each numerals from 1 to 8, and total from 4 to 10. Such compounds may be made by reacting a neoalkanoyl chloride with a suitable polyamine but, as with the monoamides, a less costly synthesis is directly from the appropriate neoalkanoic acid by reacting it with such polyamine. The melting points of the described polyamides, like those of the previously described monoamides, will normally be low, so that the products will desirably be liquids, preferably viscous, oily liquids. Such physical state is unusual for primary and secondary amides of comparable or even lower molecular weight because of strong intermolecular forces that are characteristic of the amide functionality. However, the viscous oily liquid state of the materials of the present invention is considered to be highly desirable because it is considered to improve adherence to the hair (which "adherence" may really be the result of molecular attraction) and contributes to conditioning actions. It is also important for the polyamides of this invention to be essentially water insoluble, while yet being readily distributable throughout an aqueous medium at normal use temperatures for washing laundry or treating human hair, such as in the 10 to 50° C. or 60° C. range, often preferably 20 to 45° C. or 50° C. Thus, when choosing polyamines and neoalkanoic acid reactants, selecting such reactants with desired proportions of hydrophilic and hydrophobic groups, such as ethylene oxide and propylene oxide (or butylene oxide) allows one to control the hydrophile-lipophile balance of the polyamide so that it can be a more effective antistat in the intended process or product.

It is considered that among the best polyamide components of the present antistatic compositions are those made from a neoalkanoic acid, such as neodecanoic acid, and a polyoxypropylene triamine, such as Jeffamine T-403. Other Jeffamines, such as Jeffamines D-230, D-400 and D-2,000, may also be employed to make the invented polyamides. When the polyamine is ethylene diamine or hexamethylene diamine antistatic activities with quaternary ammonium salts are also obtainable.

The Jeffamine polyamines that may be employed to manufacture the antistatic polyamides of this invention are described in a booklet entitled JEFFAMINE Polyoxypropyleneamines, published by Texaco Chemical Company and copyrighted in 1978 by Jefferson Chemical Company, Inc. Formulas of such polyamines are given at pages 2 and 3 thereof and typical physical properties for them are listed at pages 3 and 4. Uses of the Jeffamines are described throughout the booklet, primary among which is that of a component of synthetic resins, such as epoxy resins and polyurethanes. In a bibliography near the end of the booklet, at pages 61-64, textile applications of the Jeffamines and related materials are listed and summarized. None of the references, as mentioned in the Jeffamine booklet, describes or suggests polyamides of the type described herein, and the desirable characteristics thereof.

Triamides that are useful in the processes and preparations of this invention are of the formula

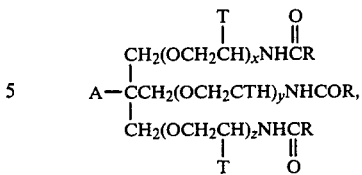

wherein A is alkyl of 1 to 20 carbon atoms or hydrogen, T is methyl or hydrogen, R is a neoalkyl of 4 to 13 carbon atoms, and x, y and z are each numerals from 1 to 8, and total 4 to 10. More preferably, A is an alkyl of 1 to 4 carbon atoms, T is methyl, R is a neoalkyl of 4 to 9 carbon atoms, and x, y and z are each numerals from 1 to 3, which total from 4 to 8. Still more preferably, A is an alkyl of 1 to 3 carbon atoms, T is methyl, R is neoalkyl of 4 to 9 carbon atoms and x, y and z are each numerals from 1 to 3, which on the average total from 4.5 to 6. Most preferably, A is ethyl, T is methyl, R is neoalkyl of 9 or about 9 carbon atoms and x, y and z are each numerals from 1 to 3, the total of which averages about 5.3. The preferred diamides of this invention are of the formula:

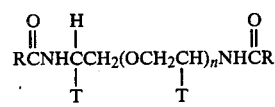

wherein T is methyl or hydrogen, R is a neoalkyl of 4 to 13 carbon atoms, and n is from 1 to 40. More preferably, T is methyl, R is neoalkyl of 4 to 9 carbon atoms and n is a numeral from 2 to 10. Still more preferably, T is methyl, R is neoalkyl of 4, 6 or 9 carbon atoms, and n is a numeral from 2 to 7. Most preferably, T is methyl, R is neoalkyl of 9 or about 9 carbon atoms and n is an average of about 5.6. Other useful diamides are those of the formula:

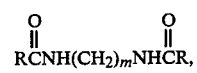

wherein R is a trialkylmethyl of 4 to 13 carbon atoms and m is 2 to 10. Preferred among such diamides are those which may be considered to be the reaction products of the reaction of a trialkylacetic or neoalkanoic acid of 5 to 10 carbon atoms with an alkylene diamine of 2 to 6 carbon atoms. Among such compounds those preferred are N,N'-ethylene-bis-neodecanoamide and N,N'-hexamethylene-bis-neodecanoamide.

It will be seen from the above formulas and descriptions of components and substituents thereof that the amine radicals of the monoamines and polyamines (including diamines) are completely converted to amide form. However, while such amides are highly preferred, it is contemplated that incompletely "amidified" polyamines which are at least ⅔ amidified may also be employed in the invented compositions as hair conditioners. They will have some of the undesirable properties of quaternary ammonium salts, in that they may be reactive with anionic detergents, but it is considered that such reaction and any resulting undesirable effects thereof will often be tolerable because only a minor proportion of the reactive amine radicals will not have been converted to non-reactive amides. Also any adverse effects due to the presence of unreacted amine groups may be ameliorated by blending with other completely amidified fiber antistats of this invention. Additionally, such amines may take the place of an equivalent proportion of quaternary ammonium salt under suitable circumstances.

Mixtures of the polyamides may be employed in any desired and effective proportions. Thus, for example, N,N'-ethylene-bis-neodecanoamide may be mixed with N,N'-hexamethylene-bis-neodecanoamide; N,N'-ethylene-bis-neodecanoamide may be mixed with N,N'-hexa-methylene-bis-neopentanoamide; the tri-neodecanoamide of Jeffamine T-403 may be mixed with the di-neodecanoamide of Jeffamine D-230; and the tri-neodecanoamide of Jeffamine T-403 may be mixed with N,N'-ethylene-bis-neodecanoamide, to mention only a few of the possible combinations. Also, 3- and 4-member and other combinations of the polyamides may be made. Such mixtures or components thereof may be mixed with monoamides, such as tallowalkyl neodecanoamide, and mixtures of the monoamides, such as 1:1 mixtures of cocoalkyl- and tallowalkyl neodecanoamides, may also be employed. Additionally, mixtures of isostearamides, such as 1:1 mixtures of cocoalkyl isostearamide (CISA) and tallowalkyl isostearamide (TISA) or mixtures of CISA and the nedecanoamide of Jeffamine T-403 in 1:2 or 1:3 proportions may be used.

The isostearamides employed in the present invention, with the quaternary ammonium salt, are usually named N-alkylisostearamides but it is to be understood that when natural sources, such as animal and vegetable materials, are used as starting materials to produce the amines which are reacted with the isostearic acid, mixtures of aliphatic amines result and often such will contain a minor proportion of unsaturated aliphatic material (alkene, such as octadecene-1) with the saturated hydrocarbyl group donor present. In this specification reference to N-alkyl isostearamide is intended to encompass such amides which contain some unsaturation, due to the amine reactant having been derived from a natural starting material containing such unsaturation.

To make it clear that unsaturated isostearamides, such as N-oleylisostearamide, may also be employed in the practice of the present invention, future references in this specification will sometimes be to N-alk(en)ylisostearamides. The N-alk(en)ylisostearamides that are useful are those wherein R' in the formula RCONHR' is a saturated or monounsaturated hydrocarbyl of 1 to 18 carbon atoms, preferably averaging 8 to 18 carbon atoms and more preferably 12 to 18 carbon atoms. Examples of such amides are those wherein R' is octyl, decyl, dodecyl, stearyl, oleyl, cocoalkyl, hydrogenated tallowalkyl or tallowalk(en)yl.

The quaternary ammonium salt(s) which is/are employed in comparatively minor proportion with the amide(s) in the compositions and processes of the present invention may be any suitable such salt but normally will preferably be a halide, such as a chloride or bromide. While many of the quaternary ammonium salts known in the art are useful in the practice of the present invention, including those known primarily for their disinfectant, emulsion stabilizing, adhesion increasing, fabric softening, anticorrosion and cosmetic (deodorant) properties, it will often be preferred to employ those known primarily for antistatic applications. Among such antistatic agents are the higher alkyl, lower alkyl substituted quaternary ammonium chlorides, such as those having at least one higher alkyl (averaging 10 to 18 carbon atoms) and at least two lower alkyls (averaging 1 to 4 carbon atoms). Often the most preferable quaternary ammonium chlorides will be di-higher alkyl, di-lower alkyl ammonium chlorides, such as distearyl dimethyl ammonium chlorides. Preferred higher alkyls (or alkenyls) of the quats are lauryl, myristyl, cetyl, oleyl and stearyl or mixtures of two or more thereof, and preferred lower alkyls are methyl and ethyl, with methyl being most preferred. Quaternary ammonium salts known for their antistatic properties include polyethoxylated quaternary ammonium salts, such as those sold under the trademark Ethoquad, alkyl dimethyl benzyl ammonium chloride, such as that sold under the tradename Genamin KD B, polyoxyethylstearyl ammonium chloride (Genamin KS 5), Nyamine SA, trimethyl lanolyl ammonium chloride and cetyl dimethylbenzyl ammonium bromide. While di-higher alkyl, di-lower alkyl ammonium halides are not listed above as being known for their antistatic properties it has been found that in the present compositions they act together with the described amide(s) to significantly improve the antistatic effects of the amides without causing the disadvantageous effects often encountered when the quaternary ammonium salt alone is employed in antistatic quantity.

In addition to the mentioned amides and quats other antistatic materials may also be present with them (and sometimes in substition for the quat), in accordance with the present invention. Thus, some amines, ethylene oxide condensation products and amides, known to have antistatic activity, may be employed to further improve the antistatic actions of the present compositions and processes. Among such are an alkyl polyethoxy amide which has been marketed as Antistat H, N,N-bis(2-hydroxyethyl) alkylamine, marketed as Antistat C-2, certain ethylene oxide condensates or polyglycol esters, and alcohol phosphates, marketed under the tradename Cirrasol. In particular, the amine antistats may in some instances be employed in replacement of at least a part, e.g. ¼ of the quat in the present compositions, without loss of antistatic effect and without the adverse affects that are often noted when larger antistatic proportions of quats are present with anionic materials, such as detergents and emulsifiers.

The antistatic compositions of this invention, which are useful in themselves or as additives to other compositions to impart antistatic effects to them comprise one part of quaternary ammonium salt and about 2 to 10 parts of amide of trialkylacetic acid and/or amide of isostearic acid. Preferably the proportion of such amide(s) to quaternary ammonium salt is in the range of 2:1 to 6:1, more preferably 3:1 to 5:1, e.g., about 4:1. In such proportions the negative characteristics of the quaternary ammonium salt (when reacted with anionic surface active agent) on a treated substrate, such as laundry fibers or human hair, are relatively slight and yet, the quat significantly improves the antistatic activity of the amide(s). When the described compositions are employed as antistatic additives to other compositions it will often be preferred that they consist of or consist essentially of the recited amide and quat in the proportions given. In highly preferred embodiments of the invention such antistatic compositions consist essentially of one part by weight of distearyldimethyl ammonium chloride and four parts by weight of tallowalkyl neodecanoamide, Jeffamine T-403 tri-neodecanoamide, Jeffamine D-203 di-neodecanoamide or N,N'-ethylene-bis-neodecanoamide.

While compositions consisting essentially of the quat and amide are often most useful as additives to other compositions to make them antistatic, the present invention also relates to such final antistatic compositions containing the quat and amide components in the described proportions, as well as to processes in which such compositions are used, which processes result in treated materials being made antistatic. The invention is also of antistatic compositions like those two-member compositions previously described, except for the presence with them of a solvent, dispersing medium, particulate filler or other substance which facilitates use of the antistatic materials. Almost any such diluent, filler, functional material or plurality thereof may be employed with the quat and amide so long as it does not objectionably interact with either of such antistatic components. The quat and amide do not react with each other and compositions containing both of them (in the absence of other materials, or in the presence of other non-reactive materials) are stable for indefinite periods of time.

A preferred antistatic composition of this invention is a detergent composition which effectively cleans laundry and makes materials washed with it antistatic. Such a composition comprises a detersive proportion of the synthetic organic detergent and a total proportion, which is capable of imparting an antistatic characteristic to laundry during washing with the detergent composition, of an antistatic amide of trialkylacetic acid and/or antistatic amide of isostearic acid, and a quaternary ammonium salt, with the proportion of such amide(s) being from 2 to 10 times that of the quat. Preferably, such detergent composition is in particulate form and comprises about 5 to 35% of synthetic organic detergent, which is anionic and of sulfate and/or sulfonate type, about 10 to 85% of builder(s) for such synthetic organic detergent, about 3 to 10% total of antistatic amide(s) and quat(s), with the amount of amide(s) in the composition being about two to six times that of the quat(s), and about 2 to 20% of moisture. In such a detergent composition it is preferred that the quat be of a proportion of from 1:3 to from 1:5 with respect to the antistatic amide(s). While a plurality of types of amides may be present, it is often preferable to utilize only one in such detergent compositions, together with a single quat.

In the mentioned detergent compositions the synthetic organic detergent is usually one or more of linear higher alkylbenzene sulfonate, branched higher alkyl benzene sulfonate, higher fatty alcohol sulfate, olefin sulfonate, paraffin sulfonate, monoglyceride sulfate, higher fatty alcohol ethoxylate sulfate, higher fatty acid sulfoester of isethionic acid, higher fatty acyl sarcoside, acyl amide of N-methyl taurine, sulfoamide of N-methyl taurine, or any mixture thereof, wherein the higher radicals are of 8 to 20 carbon atoms, usually preferably of 10 to 18 carbon atoms. In such compositions the builder present will normally be a compound from the group of polyphosphate, carbonate, bicarbonate, sesquicarbonate, silicate, sesquisilicate, citrate, nitrilotriacetate, polyacetal carboxylate, zeolite, or any mixture thereof. Such synthetic detergent and builder salts will normally be sodium salts. The amides in such detergent compositions may be any or those previously named, including those of the described Jeffamines or lower alkylene diamines (as the neoalkanoamides), or the isostearamides. Preferably the amide will be of a trialkylacetic acid of 5 to 16 carbon atoms wherein each of the alkyls of the trialkylacetic acid will be of 1 to 10 carbon atoms, and a mono-N-higher alk(en)yl amine or a polyamine of 2 to 5 amino groups, or will be a higher aliphatic isostearamide, or a mixture of any of such amides. In such compositions any of the described quaternary ammonium salts may be employed, in the proportions indicated, but it is preferred that such quaternary ammonium salt be a halide, more preferably a chloride, and the more highly preferred quaternary ammonium chlorides now known for use in such compositions are the di-higher alkyl, di-lower alkyl ammonium chlorides, such as distearyl dimethyl ammonium chloride.

Preferred detergent compositions of this invention are those wherein the synthetic organic detergent employed is sodium linear alkylbenzene sulfonate in which the alkyl group is of 12 to 15 carbon atoms, the builder is a mixture of sodium tripolyphosphate, sodium silicate, sodium carbonate and borax, the quaternary ammonium salt is di-higher alkyl, di-lower alkyl ammonium chloride and preferred percentages of such components, antistatic amide and moisture are 8 to 20% of sodium linear alkylbenzene sulfonate, 15 to 40% of sodium tripolyphosphate, 3 to 10% of sodium silicate, 2 to 10% of sodium carbonate, 0.3 to 3% of borax, 0.5 to 2% of di-higher alkyl, di-lower alkyl ammonium chloride, 2 to 8% of antistatic amide (as previously described in the specification) and 1 to 15% of moisture. More preferred proportions of more preferred components are 10 to 18% of sodium linear tridecylbenzene sulfonate, 20 to 30% of sodium tripolyphosphate, 4 to 9% of sodium silicate, of $Na_2O:SiO_2$ ratio of 1:2.4, 3 to 7% of sodium carbonate, 0.5 to 2% of borax, 0.6 to 1.5% of distearyl dimethyl ammonium chloride, 3 to 6% of the antistatic amide(s), and 2 to 12% of moisture.

While it is a prime purpose of the present invention to make built or heavy duty synthetic organic detergent compositions which can wash laundry containing synthetic organic polymeric fibrous materials, such as nylons and polyesters, without such materials accumulating static charges while being dried in an automatic laundry dryer, which is usually of the tumbling type, the invented antistatic compositions and the components of such compositions, when employed in other preparations, also usefully inhibit static charge accumulations on a variety of substrates, including human hair, and when applied onto such other substrates and onto laundry from other compositions and by other mechanisms than that of washing in a detergent solution containing the combination of antistatic materials of the invention. Thus, shampoos for washing human hair will decrease flyaway action of the shampooed hair when they incorporate an antistatic proportion of antistatic amide of trialkylacetic acid and/or antistatic amide of isotearic acid, together with a quaternary ammonium salt, with the proportion of amide(s) present being two to ten times that of the quaternary ammonium salt(s). The concentration of the total of antistatic amide and quat will normally be within the range previously given for such concentration in built laundry detergent compositions, 3 to 10%, but this may be adjusted to suit the particular shampooing application. Similarly, rinses, gels, lotions and other preparations intended for application to the hair may also include the invented combination at the same concentration as for the shampoos. The shampoos and other hair products mentioned will normally be in aqueous media, with such aqueous or aqueous alcohol medium usually comprising 50 to 90% of such compositions. The shampoos may contain from 3 to 25% of suitable synthetic organic detergent, such as sodium lauryl sulfate, sodium myristyl sulfate, sodium cocomonoglyceride sulfate or mixtures of such materials. Other materials that may be present in the invented antistatic hair preparations include dyes, fluorescent brighteners, perfumes, buffers, lanolin and lanolin derivatives, solvents, cosolvents, antifreezes, suspending agents, emulsifiers and hydrotropes.

Another use of the present antistatic compositions and the components thereof is in dryer products, which often include a substrate material, such as paper, cloth or sponge, having thereon or impregnated therein an antistatic amide and a quat of this invention, in such quantity (which may be from 10 to 400% by weight of the substrate material) as to be sufficient to transfer to laundry being dried in sufficient amount to render such laundry antistatic. The invented composition or the components thereof may be applied directly to a suitable substrate of the type described or may be dissolved or dispersed in a suitable medium, such as a higher fatty alcohol, or a waxy lower alkylene oxide polymer, which may be deposited onto the substrate together with the antistatic composition or antistatic component.

The invented compositions and the amide and quat components thereof may also be employed in various other antistatic preparations and in compositions which are intended for applications to materials which tend to accumulate static charges. Thus, they may be utilized in preparations for cleaning or deodorizing rugs, as well as in or on products to remove static charges from polymeric materials or articles which are susceptible to static charge accumulation, such as clothes brushes, phonograph record cleaners and recording tape guides.

Various compositions within the invention have been described above. Also within the invention are processes in which such compositions are employed. In one such process, that of washing laundry and reducing static charges thereon after automatic laundry dryer drying of the laundry, the laundry is washed in wash water containing from 0.05 to 0.4% of a detergent composition of this invention or of 0.002 to 0.02 percent of the antistats of such composition, after which the laundry is rinsed and dried in an automatic laundry dryer. It is found that after such drying the laundry is substantially free of static charge, despite a substantial content in the laundry (often more than 40% of the total laundry) of synthetic organic polymeric fibers. Control laundry of the same general composition, and washed with the same detergent, except that the antistatic compounds of this invention were omitted from it, exhibits the negative attributes of electrostatic charge accumulation thereon, clinging to various surfaces, including the body of the wearer, and sometimes crackling with electric discharges when rubbed.

The following examples illustrate but do not limit the invention. Unless otherwise indicated all parts are by weight and all temperatures are in ° C. in the examples and elsewhere in this specification, and in the appended claims.

EXAMPLE 1

| Component | Percent |
|---|---|
| Sodium linear tridecylbenzene sulfonate | 13.4 |
| Sodium tripolyphosphate | 24.0 |
| Sodium silicate (Na$_2$O:SiO$_2$ = 1:2.4) | 6.3 |
| Sodium carbonate | 4.5 |
| Borax | 1.0 |

-continued

| Component | Percent |
|---|---|
| Fluorescent brighteners | 0.3 |
| Methyl cellulose | 0.5 |
| Sodium carboxymethyl cellulose | 0.2 |
| Sodium sulfate | 49.6 |
| Perfume | 0.2 |
| | 100.0 |

A detergent composition of the above formula is made by spray drying an aqueous crutcher mix of 60% solids content in a conventional countercurrent spray drying tower to produce spray dried detergent beads, less perfume, which beads are subsequently perfumed by spraying onto the surfaces thereof the formula proportion of liquid perfume. The product is screened so that the particle sizes thereof are in the range of No's. 10 to 100, U.S. Sieve Series.

Antistatic compositions of the present invention are made by melting or fusing together four parts of amide and one part of quaternary ammonium salt. Four different antistatic compositions were made, of the following formulas: (A) four parts by weight of ethylene bis-neodecanoamide (E-Dec) and one part of distearyl dimethyl ammonium chloride (DSDMAC); (B) four parts of polyoxypropylene-bis-neodecanoamide (J-Dec, made from Jeffamine D-230 and neodecanoic acid) and one part of DSDMAC; (C) four parts of tallowalkyl neodecanoamide (T-Dec) and one part of DSDMAC; and (D) four parts of cocoalkyl isostearamide (CISA) and one part of DSDMAC. The various amides were made by the condensation reactions described in the foregoing specification, which are also described in U.S. patent applications Ser. Nos. 716,871, filed Mar. 27, 1985, and 734,508, filed May 16, 1985, of the present inventions entitled Antistatic Agents which are Multiamides and U.S. Pat. No. 4,497,715.

Five parts of each of the antistatic compositions, in liquid form, are sprayed onto 95 parts of the detergent composition, to make four different antistatic detergent composition formulas. Also, for controls five parts of the respective amides are each sprayed onto separate 95 parts portions of the detergent composition. A further control is the detergent composition, without any antistatic additive.

In addition to testing of the fabric softening detergent compositions described, the antistatic compositions and the components of such compositions are also tested by direct additions in "particles" (which may be droplets or oily solids, depending on the amide material, and may be powders, for the quats) at 25° C. to wash waters at 49° C., containing a detersive concentration of the detergent composition (0.15%). In such cases the proportion of antistatic compositions or total percentage of components thereof (amide plus quat) is 0.0079%.

The invented antistatic detergent compositions are tested for both antistatic effect and cleaning power, using various different types of fabrics, some of which are first soiled or stained with different test soils. Antistatic effects of the antistat materials are evaluated by washing the test fabrics in a top loading Whirpool washing machine and drying them in an electric automatic clothes dryer of the tumbling type, after which they are tested for static accumulations. A balanced load is employed in the washing operations with antistat effect test swatches and with soil removal index swatches being present, the latter swatches being used to permit checking on any possible negative effects of the antistat compositions on soil removal properties of the detergent composition. The balanced load in the washing machine weighs five pounds and consists of ⅓ cotton terry facecloths; ⅓ cotton percale swatches (14 by 15 inches); and ⅓ of 65% Dacron: 35% cotton swatches (14×15 inches, without durable press finish). The test fabrics used for antistatic effect measurement measure 14 inches by 15 inches and for each test include one each of: 65% Dacron—35% cotton permanent press; Banlon; Dacron double knit twill; acetate jersey; and nylon tricot. The soil removal index swatches measured 3×6 inches and four of each type (for a total of twenty) are present with the balanced laundry in each test. The five different types of such test swatches are: Test Fabrics Inc. soil on nylon cloth (TFN); Test Fabrics Inc. soil on cotton cloth (TFC); Piscataway (New Jersey) clay on cotton cloth (PCC); Piscataway clay on 65% Dacron—35% cotton cloth (PCDC); and EMPA 101 oily soil on 65% Dacron—35% cotton cloth (EMPA).

After thorough cleaning of the washers and dryers, using 3A denatured alcohol, followed by air drying, the washing machine is set for a 14 minute wash cycle, using 17 gallons of water at 49° C. (120° F.). This wash is one utilizing the normal machine cycle, including a rinse with cold tap water. The detergent composition, containing the antistat composition of amide and quat, is added to the wash water after the machine is filled, the machine is allowed to agitate for about 10 seconds and then the ballast load and the various test and soil removal index swatches are separately added, while agitation is continued. Subsequently, after completion of the washing (and rinsing) the various fabrics are removed and placed in the electric dryer, where they are dried over a period of about two hours. The test swatches and two terry towels from the ballast are then tumble dried for an additional ten minutes, following which the test swatches are evaluated for static cling. Prior to instrumental static measurements the test swatches are hung in a low humidity room (25% relative humidity) overnight. To determine the static charges on the test materials, after they have been washed with the antistatic detergent composition (or a control) all of the static test swatches are sequentially rubbed in a controlled manner, at particular locations thereof, with wool, under controlled conditions, at a relative humidity in the range of 25 to 30%, after which the electrostatic charges on the swatches are measured at each of the locations and the measured electrostatic charges are averaged for each swatch. The resulting averages for the same types of swatches are again averaged, resulting in static indexes (measured in kilovolts) for the antistat compositions tested on each material. A total static index for the antistatic composition (or for the antistatic detergent composition) is obtained by adding the indexes for each of the five test materials. The higher the total static index, the greater is the static accumulated, and the less effective is the antistat tested.

The soil removal index (SRI) is calculated from differences between reflectometer readings, of test swatches before and after washings. The greater such differences, the better the soil removal from the test material. Utilizing a formula which weights the cleaning effects of detergent compositions on the previously mentioned soils, the soil removal indexes are calculated from the various reflectometer reading differences.

Table 1 shows the static indexes, in kilovolts, for the five types of fabrics washed, for each of the four invented 4% amide/1% quat compositions, for each of four all-amide (5%) control compositions, and for a detergent composition containing neither amide nor quat (0% of each). The sum line indicates the total of the individual static indexes. From this table it is apparent that the antistatic compositions and the antistatic detergent compositions of this invention, when employed in washing mixed static-prone fabrics which contain synthetic organic polymeric fibrous materials of the types described, are superior to secondary control antistatic compositions and antistatic detergent compositions in which the quat is replaced by amide, which control compositions are far superior in antistatic actions to primary control detergent compositions containing neither amide nor quat.

Table 2 shows the soil removal indexes (SRI) for the base detergent composition, containing no amide and no quat, and three amide-quat combinations and three control compositions containing 5% of each of the amide (the fourth tests were not run). From this table it is seen that there is relatively little adverse affect on the cleaning power of the detergent composition due to the presence therein of the 1% of quaternary ammonium salt (distearyl dimethyl ammonium chloride.)

TABLE 1

Antistatic Indexes (Kilovolts)

| Antistatic Composition | Fabrics | | | | | Total Index |
|---|---|---|---|---|---|---|
| | 65% Dacron/35% Cotton | Banlon | Dacron Double Knit | Acetate | Nylon | |
| 4% E-DEC* + 1% DSDMAC* | 2.3 | 5.0 | 2.1 | 2.7 | 1.7 | 13.8 |
| 5% E-Dec | 5.4 | 10.3 | 0.7 | 3.8 | 8.6 | 28.8 |
| 4% J-Dec* + 1% DSDMAC | 1.4 | 1.9 | 0.7 | 2.2 | 2.4 | 8.6 |
| 5% J-Dec | 4.3 | 13.3 | 0.5 | 3.9 | 9.0 | 31.0 |
| 4% T-Dec* + 1% DSDMAC | 3.2 | 3.9 | 3.1 | 1.8 | 1.5 | 13.5 |
| 5% T-Dec | 3.4 | 13.8 | 3.3 | 3.7 | 6.2 | 30.4 |
| 4% CISA* + 1% DSDMAC | 4.0 | 5.8 | 3.2 | 1.0 | 0.8 | 14.8 |
| 5% CISA | 4.2 | 15.0 | 1.5 | 4.3 | 4.0 | 29.0 |
| 0% amide and | 4.5 | 18.0 | 11.1 | 4.3 | 14.6 | 52.5 |

TABLE 1-continued

| | Antistatic Indexes (Kilovolts) | | | | | |
|---|---|---|---|---|---|---|
| | Fabrics | | | | | |
| Antistatic Composition | 65% Dacron/35% Cotton | Banlon | Dacron Double Knit | Acetate | Nylon | Total Index |
| 0% Quat | | | | | | |

*E-Dec = ethylene-bis-neodecanoamide
J-Dec = diamide of Jeffamine D-230 and neodecanoic acid
T-Dec = tallowalkyl neodecanoamide
CISA = cocoalkyl isostearamide
DSDMAC = distearyl dimethyl ammonium chloride While the presence of the amide may have a slight improving effect on the SRI and the presence of the quat may have a slight negative effect, as a practical matter the effects are almost indistinguishable to the consumer. On the contrary, when the percentage of quat is increased to more than 2%, in the detergent composition (or more than 0.003% in the wash water), and especially if it is increased to as much as 4 or 5%, appreciable negative effects on cleaning will be noticeable to the consumer and correspondingly, differences in the SRI's will be much greater. Less than 2% of DSDMAC or of other quat or cationic antistatic agent in the detergent compositions used to wash laundry, as described, will not normally be sufficient to render the washed laundry and test swatches antistatic.

TABLE 2

| | Soil Removal Indexes | |
|---|---|---|
| Antistatic Composition | Absolute Value | Difference Between Absolute Values for Test and Control (0% Amide, 0% Quat) |
| 4% E-Dec + 1% DSDMAC | 210 | −2 |
| 5% E-Dec | 222 | +10 |
| 4% J-Dec + 1% DSDMAC | 208 | −4 |
| 5% J-Dec | 214 | +2 |
| 4% T-Dec + 1% DSDMAC | 205 | −7 |
| 5% T-Dec | 213 | +1 |
| 0% Amide, 0% DSDMAC | 212 | — |

When the antistatic compositions of this invention, as described in the foregoing working example, are added to the described wash water (containing the detergent composition less antistat composition), instead of being incorporated in the detergent composition, the same antistatic and detersive results are obtained. Similarly, when the components of the antistatic compositions are separately added to the wash water the same results are also obtainable. When other quaternary ammonium salts are employed in place of the DSDMAC, such as stearyl benzyl dimethyl ammonium chloride, cetyl trimethyl ammonium bromide, dicocoalkyl dimethyl ammonium chloride, N-cetyl-ethyl morpholinium ethosulfate, polyoxyethyl stearyl dimethyl ammonium chloride and trimethyl lanolyl ammonium chloride, and when the amide(s) are replaced by corresponding neopentaoamide, neoheptoamide, neododecanoamide, Tri-Dec (which is the triamide of Jeffamine T-403 and neodecanoic acid), N,N′-hexamethylene-bis-neodecanoamide, cocoalkyl neodecanoamide or tallowalkyl isostearamide, essentially the same results are obtainable, with the invented antistatic compositions being better in antistatic activity than corresponding weights of all-amide controls and with the invented compositions not objectionably diminishing the detergencies of the washing compositions employed (in which other synthetic anionic organic sulfated and sulfonated detergents may be substituted for the sodium linear alkylbenzene sulfonate).

When mixtures of the invented compositions are utilized, such as in compositions comprising 2% of E-Dec and 2% of T-Dec with 1% of DSDMAC, or 1% of TISA (tallowalkylisostearamide), 2% of CISA and 1% of J-Dec, with 1% of DSDMAC, similar antistatic and detersive activities result.

When the detergent composition utilizes a different anionic detergent, such as a detergent composition comprising 10% of sodium linear dodecylbenzene sulfonate, 5% of sodium lauryl alcohol sulfate, 24% of sodium tripolyphosphate, 5% of sodium silicate, 5% of sodium carbonate, 40% of sodium sulfate, 1% of minor adjuvants and the balance of moisture, with the invented antistatic compositions and the proportions thereof being the same as given in Table 1, substantially the same antistatic and detersive effects are obtained, with the antistatic effects being superior to those for all-amide controls and being much superior to that of the detergent composition alone. Similarly, when a primarily nonionic detergent composition is utilized instead of that of Example 1, such as a composition made by producing spray dried beads comprising 20 parts each of sodium carbonate, sodium bicarbonate, and zeolite 4A, and 10 parts of bentonite, 8 parts of water and 2 parts of adjuvants, and spraying onto the surfaces of such spray dried beads (of particle sizes like those of the product previously described in Example 1) 20 parts of nonionic detergent (Neodol 23-6.5, which is the condensation product of a higher fatty alcohol of an average of 12 to 13 carbon atoms, and about 6.5 moles of ethylene oxide per mole of higher fatty alcohol), with the antistatic compositions and proportions being the same, similar improvements in antistatic actions are observable over a control in which no antistatic compounds are present (detergent only) and over controls containing amide only (in total proportion equal to amide plus quat in the experimental or invented compositions).

EXAMPLE 2

A shampoo is made by mixing together 20 parts of ammonium monoglyceride sulfate, 30 parts of ethanol, 48 parts of water (deionized) and 2 parts of adjuvants (thickener, fluorescent brightener, fungicide and antioxidant). To 99 parts of such shampoo there is added one part of antistatic composition of this invention, which is made up of 0.8 part of CISA and 0.2 part of DSDMAC.

Hair shampooed with the described antistatic shampoo is noticeably less prone to the accumulation of static charges, with resulting "flyaway" characteristics, than hair washed with a control shampoo, which is the same shampoo as described above, without the antistatic composition. Also, hair washed with the described antistatic shampoo is superior in antistatic properties to hair washed with an antistatic shampoo containing 1 part of CISA, no part(s) of quat and 99 parts of the shampoo composition (no antistat). Hair tresses are subjected to controlled laboratory shampooings with the basic shampoo and with the controls, using one part by weight of shampoo per two parts of by weight of hair tress, followed by rinsing with 41° C. tap water, combing and blow drying, after which the conditions of the tresses are observed by skilled operators and the tresses are subjected to static accumulation tests in which, after drying, they are combed with a hard rubber comb and then measured for static charges. By both visual observation and charge measurement tests the tresses treated with the invented antistatic shampoo containing the antistatic composition of this invention is superior to the shampoo-only control and to the shampoo with amide control in inhibiting static charge accumulation on the shampooed hair. The hair shampooed with the shampoo containing all-CISA as the antistatic agent (with 0.2 part of CISA replacing 0.2 part of DSDMAC), is better in static charge collection inhibiting characteristics than the basic or primary control (the shampoo alone, without any antistat) but is inferior to the shampoo containing the invented antistat composition.

When, instead of the antistatic composition being incorporated into a shampoo, it is dissolved in an appropriate aqueous alcoholic medium, such as one comprising two parts of ethanol per part of water, and is applied to shampooed hair and hair tresses in the same manner as described previously in this example, but as a rinse, rather than as a shampoo, similar results are obtained, but the static charge accumulation inhibition is better with the rinse than with the shampoo.

In both the shampoos and rinses described the other amide antistats described in this specification may be substituted for the CISA and the other quats may be substituted for the DSDMAC, and the results obtained will be essentially the same. Similarly, other detergents, such as previously described in the specification, may be substituted for the ammonium monoglyceride sulfate, and other aqueous rinse media may be employed, such as those containing different percentages of water and ethanol, and those containing other co-solvents of types known in the hair rinse art, and similar effects will be observable.

Also, proportions of components may be changed within the ranges described in the specification and comparable desirable antistatic action on the hair will result from both the invented shampoos and rinses.

EXAMPLE 3

Dryer sheets are made by preparing an antistatic composition of this invention somewhat like that described in Example 1 (four parts of J-Dec and one part of DSDMAC), melting it and impregnating an absorbent paper towel sheet with it to the extent of two parts by weight of the antistatic composition and one part by weight of the paper towel material. After washing of a load of ordinary mixed, soiled laundry (six pounds), containing nylon, acetate and polyester fabrics, it is dried in an automatic electric laundry dryer of the tumbling type with a sheet of such treated toweling, measuring approximately 11 inches by 11 inches, also being added to the dryer, wherein during the tumble drying of the laundry the antistatic composition or a part thereof is transferred to the laundry, rendering it antistatic. As in Examples 1 and 2, other amides and quats can be substituted, and the results will be similar. Also, proportions and application rates may be adjusted, within the limits previously given, and good antistatic effects will be transmitted to the dried laundry. Polyurethane sponge sheets may replace the paper.

The antistatic compositions of this invention may also be applied to the drying laundry or to materials to be made antistatic, by spraying them carefully onto the surfaces thereof, and they may be applied to the hair from a comb, onto the teeth of which they had been previously deposited. In such applications the invented compositions are superior in antistatic effects on synthetic organic polymer-containing laundry, compared to equal applications of amide-only antistat.

The invention has been described with respect to various illustrations and examples thereof but is not be limited to these because it is evident that one of skill in the art with the present specification before him will be able to utilize substitutes and equivalents without departing from the invention.

What is claimed is:

1. An antistatic composition which consists essentially of 2 to 6 parts by weight of tallowalkyl neodecanoamide and one part by weight of distearyl dimethyl ammonium chloride.

2. An antistatic composition comprising 2 to 6 parts by weight of

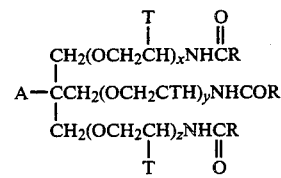

wherein A is an alkyl of 1 to 4 carbon atoms, T is methyl, R is a neoalkyl of about 4 to 9 carbon atoms, and x, y and z are numerals from 1 to 3, which total from 4 to 8, and one part by weight of a quaternary ammonium chloride which includes at least one higher alkyl or higher alkenyl group of 10 to 18 carbon atoms, and at least one lower alkyl group of 1 to 4 carbon atoms.

3. A composition according to claim 2 wherein, A is ethyl, R is neoalkyl of about 9 carbon atoms, T is methyl, and x, y and z total an average of about 5.3, and the quaternary ammoniun chloride is distearyl dimethyl ammonium chloride.

4. An antistatic composition which consists essentially of 2 to 6 parts by weight of

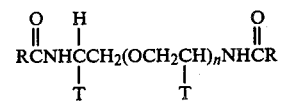

wherein T is methyl or hydrogen, R is a trialkyl methyl of 4 to 13 carbon atoms and n is from 1 to 40, and one part by weight of a quaternary ammmonium chloride which includes at least one higher alkyl or higher alkenyl group of 10 to 18 carbon atoms, and at least one lower alkyl group of 1 to 4 carbon atoms.

5. A composition according to claim 4 wherein T is methyl, R is neoalkyl of 4 to 9 carbon atoms and n is a numeral from 2 to 10.

6. A composition according to claim 5 wherein T is methyl, R is a neoalkyl of about 9 carbon atoms and n is an average of about 2.3, and the quaternary ammonium chloride is distearyl dimethyl ammonium chloride.

7. An antistatic composition comprising 2 to 10 parts by weight of a diamide of a neoalkanoic acid of 5 to 10 carbon atoms with an alkylene diamine of 2 to 6 carbon atoms and one part by weight of a quaternary ammonium halide.

8. A composition according to claim 7 wherein the diamide is N,N'-ethylene-bis-neodecanoamide and the quaternary ammonium halide is distearyl dimethyl ammonium chloride.

9. A detergent composition which effectively cleans laundry and makes materials washed with it antistatic, which comprises a detersive proportion of a synthetic organic detergent and a total proportion, which is antistatic characteristic imparting to laundry during washing with the detergent composition, of an antistatic amide of trialkylacetic acid, which amide is of the formula

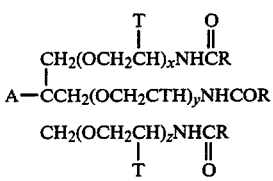

wherein A is ethyl, R is neoalkyl of about 9 carbon atoms, T is methyl, and x, y and z are each numerals from 1 to 3, which total an average of about 5.3, and distearyl dimethyl ammonium chloride, wherein 2 to 6 parts by weight of such amide is present in the detergent composition per one part by weight of distearyl dimethyl ammonium chloride.

10. A detergent composition which effectively cleans laundry and makes materials washed with it antistatic, which comprises a detersive proportion of a synthetic organic detergent and a total proportion, which is antistatic characteristic imparting to laundry during washing with the detergent composition, of an antistatic amide of trialkylacetic acid, which amide is of the formula

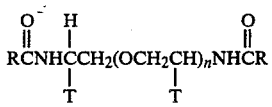

wherein T is methyl, R is neoalkyl of about 9 carbon atoms and n is an average of about 2.3, and distearyl dimethyl ammonium chloride, wherein 2 to 6 parts by weight of such amide is present in the detergent composition per one part by weight of distearyl dimethyl ammonium chloride.

11. A detergent composition which effectively cleans laundry and makes materials washed with it antistatic, which comprises a detersive proportion of a synthetic organic detergent and a total proportion, which is antistatic characteristic imparting to laundry during washing with the detergent composition, of an antistatic amide of trialkylacetic acid, which amide is a diamide of a neoalkanoic acid of 5 to 10 carbon atoms with an alkylene diamine of 2 to 6 carbon atoms, and distearyl dimethyl ammonium chloride, wherein 2 to 6 parts by weight of such amide is present in the detergent composition per one part by weight of distearyl dimethyl ammonium chloride.

12. A detergent composition which effectively cleans laundry and makes materials washed with it antistatic, which comprises a detersive proportion of a synthetic organic detergent and a total proportion, which is antistatic characteristic imparting to laundry during washing with the detergent composition, of an antistatic amide of isostearic acid, which amide is a higher alkyl or higher alkenyl isostearamide or mixture thereof, and distearyl dimethyl ammonium chloride, wherein 2 to 6 parts by weight of such amide is present in the detergent composition per one part by weight of distearyl dimethyl ammonium chloride.

13. A composition according to claim 12 wherein the isostearamide is cocoalkyl isostearamide and the quaternary ammonium chloride is distearyl dimethyl ammonium chloride.

14. A detergent composition which effectively cleans laundry and makes materials washed with it antistatic, which comprises 8 to 20% sodium linear alkylbenzene sulfonate wherein the linear alkyl is of 12 to 15 carbon atoms, 15 to 40% of sodium tripolyphosphate, 3 to 10% of sodium silicate, 2 to 10% of sodium carbonate, 0.3 to 3% of borax, 0.5 to 2% of distearyl dimethyl ammonium chloride, 2 to 8% of antistatic amide which is a monoamide of a trialkylacetic acid of 5 to 16 carbon atoms and a mono-N-higher alkylamine, a monoamide of a trialkylacetic acid of 5 to 16 carbon atoms and a mono-N-higher alkenylamine, wherein the higher alkyl and higher alkenyl are linear and of 12 to 18 carbon atoms, a polyamide of trialkylacetic acid and polyamine, wherein the trialkylacetic acid moieties are of 2 to 10 carbon atoms in each of the alkyl thereof, the sum of the carbon atoms of the alkyls of each of the trialkylacetic acid moieties is from 3 to 12, and each of the polyamine moieties is a diamine or triamine moiety with alkylene group(s) of 2 to 10 carbon atoms and/or polyoxyalkylene alkylene group(s) connecting the amide groups of the polyamide, with the oxyalkylene of the polyoxyalkylene group(s) being of 2 to 4 carbon atoms, with the number of such groups in each polyoxyalkylene group being from 1 to 40, and with the alkylene group of the polyoxyalkylene alkylene being of 1 to 10 carbon atoms, or a higher alkyl or higher alkenyl isostearamide, wherein the higher alkyl and higher alkenyl are each linear and of 12 to 18 carbon atoms, or a mixture of any of such amides, wherein 2 to 6 parts by weight of such amide is present in the detergent composition per one part by weight of distearyl dimethyl ammonium chloride, and 1 to 15% of moisture, with the proportion of such amide(s) to distearyl dimethyl ammonium chloride being from 2 to 6 parts to one by weight.

15. A process of washing laundry and reducing static charges thereon which otherwise could be present after automatic laundry dryer drying of the laundry, which comprises washing such laundry in wash water containing from 0.05 to 0.4% of a composition which comprises a detersive proportion of a synthetic organic detergent and a total proportion which is antistatic characteristic imparting to laundry during washing with the detergent composition, of an antistatic amide of trialkylacetic acid, which amide is a monoamide of a trialkylacetic acid of 5 to 16 carbon atoms and a mono-N-higher alkyl amine wherein the higher alkyl is linear and of 12 to 18 carbon atoms, a monoamide of a trialkylacetic acid of 5 to 16 carbon atoms and a mono-N-higher alkenyl amine wherein the higher alkenyl is linear and of 12 to 18 carbon atoms, a polyamide of one of the formulas

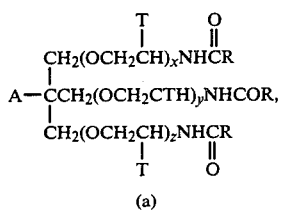

(a)

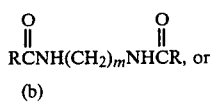

(b)

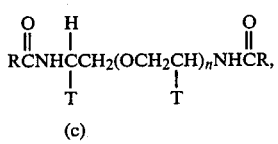

(c)

wherein A is alkyl of 1 to 20 carbon atoms or hydrogen, T is methyl or hydrogen, R is trialkylmethyl of 4 to 13 carbon atoms, m is 2 to 10, n is 1 to 40, and x, y and z are each numerals from 1 to 8, and total from 4 to 10, N-higher alkyl isostearamide wherein the higher alkyl is linear and of 12 to 18 carbon atoms, and N-higher alkenyl isostearamide wherein higher alkenyl is linear and of 12 to 18 carbon atoms, and a quaternary ammonium salt, with the proportion of such amide(s) being from 2 to 10 times, by weight, that of quaternary ammonium salt, rinsing the washed laundry and drying it in an automatic laundry dryer.

16. An antistatic composition comprising 2 to 6 parts by weight of monoamide of a trialkylacetic acid wherein the sum of the numbers of carbon atoms in the alkyls of the trialkylacetic acid is from 3 to 12, and a mono-N-higher alkylamine wherein the alkyl is linear and of 12 to 18 carbon atoms, a monoamide of such a trialkylacetic acid and a mono-N-higher alkenylamine wherein the alkenyl is linear and of 12 to 18 carbon atoms, or a mixture of such amides, and one part by weight of a quaternary ammonium chloride which includes at least one higher alkyl or alkenyl group, of 10 to 18 carbon atoms, and at least one lower alkyl group, of 1 to 4 carbon atoms.

17. A composition according to claim 16 wherein the monoamide is of a mono-N-higher alkyl amine or mono-N-higher alkenyl amine wherein the higher alkyl or alkenyl is of an average of 12 to 18 carbon atoms, and a trialkylacetic acid of 10 carbon atoms.

18. A detergent composition which effectively cleans laundry and makes materials washed with it antistatic, which comprises a detersive proportion of a synthetic organic detergent and a total proportion, which is antistatic characteristic imparting to laundry during washing with the detergent composition, of an antistatic amide of a trialkylacetic acid of about ten carbon atoms and a mono-N-higher alkyl amine, an antistatic monoamide of a trialkylacetic acid of about ten carbon atoms and a mono-N-higher alkenyl amine wherein the higher alkyl and higher alkenyl of the amines are of an average of 12 to 18 carbon atoms, or a mixture of such amides, and distearyl dimethyl ammonium chloride, wherein 2 to 6 parts by weight of such amide(s) is present in the detergent composition per one part by weight of distearyl dimethyl ammonium chloride.

* * * * *